United States Patent
Fahad et al.

(10) Patent No.: US 11,626,626 B2
(45) Date of Patent: Apr. 11, 2023

(54) LITHIUM-ION BATTERY IMPENDING FAILURE DETECTION

(71) Applicants: SERINUS LABS, INC, Berkeley, CA (US); THE REGENTS OF THE UNIVERSITY OF CALIFORNIA, Oakland, CA (US)

(72) Inventors: Hossain Mohammad Fahad, Berkeley, CA (US); Ali Javey, Berkeley, CA (US)

(73) Assignee: Serinus Labs, Inc., Berkeley, CA (US)

( * ) Notice: Subject to any disclaimer, the term of this patent is extended or adjusted under 35 U.S.C. 154(b) by 0 days.

(21) Appl. No.: 17/892,622

(22) Filed: Aug. 22, 2022

(65) Prior Publication Data

US 2022/0393258 A1    Dec. 8, 2022

Related U.S. Application Data

(63) Continuation of application No. PCT/US2021/018879, filed on Feb. 19, 2021.
(Continued)

(51) Int. Cl.
*H01M 10/48* (2006.01)
*G01N 33/00* (2006.01)
(Continued)

(52) U.S. Cl.
CPC ........ *H01M 10/48* (2013.01); *G01N 33/0031* (2013.01); *G01N 33/0063* (2013.01); *G08B 21/12* (2013.01); *H02J 7/0031* (2013.01)

(58) Field of Classification Search
None
See application file for complete search history.

(56) References Cited

U.S. PATENT DOCUMENTS 4,410,632 A    10/1983  Dilley et al.
10,862,323 B2 * 12/2020  Banos .................... A61H 11/00
(Continued)

FOREIGN PATENT DOCUMENTS

WO    WO-2020120780 A1 *  6/2020  .......... H01M 10/425

OTHER PUBLICATIONS

International search report for International application No. PCT/US21/18879, dated Apr. 20, 2021.

*Primary Examiner* — Jermele M Hollington
(74) *Attorney, Agent, or Firm* — Quinn IP Law

(57) ABSTRACT

A battery management system configured to detect impending failure of a lithium-ion battery cell includes a sensor array microchip. The microchip includes a plurality of silicon chemical-sensitive field effect transistors (CS-FETs) configured to detect multiple distinct gases vented by the lithium-ion battery cell. The battery management system also includes a cell monitoring unit (CMU) configured to receive from at least one of the CS-FETs data indicative of a detected amount of gas vented by the lithium-ion battery cell. The CMU is also configured to compare the data indicative of the detected amount of the vented gas to a predetermined threshold amount of the subject vented gas programmed into the CMU. The CMU is further configured to trigger a signal indicative of impending failure of the lithium-ion battery cell when the detected amount of the vented gas exceeds the predetermined threshold amount of the subject vented gas.

20 Claims, 4 Drawing Sheets

Related U.S. Application Data

(60) Provisional application No. 62/979,322, filed on Feb. 20, 2020.

(51) Int. Cl.
    *G08B 21/12*    (2006.01)
    *H02J 7/00*     (2006.01)

(56) References Cited

U.S. PATENT DOCUMENTS

| | | | |
|---|---|---|---|
| 11,489,229 B1* | 11/2022 | Skroski | H01M 10/613 |
| 11,567,145 B2* | 1/2023 | Liu | G01R 31/3842 |
| 2006/0240588 A1 | 10/2006 | Conley et al. | |
| 2010/0102975 A1 | 4/2010 | Vossmeyer et al. | |
| 2014/0342193 A1 | 11/2014 | Mull et al. | |
| 2015/0064514 A1 | 3/2015 | Wu et al. | |
| 2017/0294686 A1* | 10/2017 | Arnold | H01M 10/425 |
| 2018/0062210 A1* | 3/2018 | Kim | H01M 10/0525 |
| 2020/0266405 A1* | 8/2020 | Pokora | H01M 10/0525 |
| 2022/0077515 A1* | 3/2022 | Leyvi | H01M 10/482 |

\* cited by examiner

LITHIUM-ION BATTERY IMPENDING FAILURE DETECTION

CROSS-REFERENCE TO RELATED APPLICATION(S)

This application is a continuation of International Application Serial No. PCT/US 21/18879 filed Feb. 19, 2021, which claims the benefit of U.S. Provisional Application Ser. No. 62/979,322 filed Feb. 20, 2020, all of which are hereby incorporated by reference in their entirety.

INTRODUCTION

The present disclosure generally relates to a system and a method for detection of impending failure of a lithium-ion battery cell.

An electrical energy storage or battery system or array may include a plurality of battery cells in relatively close proximity to one another. A plurality of battery cells may be assembled into a battery stack or module, and a plurality of battery modules may be assembled into a battery pack. Batteries may be broadly classified into primary and secondary batteries. Primary batteries, also referred to as disposable batteries, are intended to be used until depleted, after which they are simply replaced with new batteries. Secondary batteries, more commonly referred to as rechargeable batteries, employ specific high-energy chemistries permitting such batteries to be repeatedly recharged and reused, therefore offering economic, environmental and ease-of-use benefits compared to disposable batteries.

Rechargeable batteries may be used to power such diverse items as toys, consumer electronics, and motor vehicles. Particular chemistries of rechargeable batteries, such as lithium-ion cells, as well as external factors, may, in extreme cases, cause internal reaction rates generating significant amounts of thermal energy, which may result in a thermal event. As internal reactions in rechargeable batteries accelerate, many such batteries also vent gases in advance of catastrophic battery failure. Rechargeable battery safety is a significant concern in a wide variety of applications, such as motor vehicles, aviation, and consumer electronic devices like smartphones and laptops. Safety concerns are especially poignant in electric vehicles, as demand for fast charging and long driving range vehicles is growing, thereby increasing a number of battery cells inside the subject vehicle.

SUMMARY

A battery management system configured to detect impending failure of a lithium-ion battery cell includes a sensor array microchip. The microchip includes a plurality of silicon chemical-sensitive field effect transistors (CS-FETs) configured to detect multiple distinct gases vented by the lithium-ion battery cell. The battery management system also includes a cell monitoring unit (CMU) configured to receive from at least one of the CS-FETs data indicative of a detected amount of gas vented by the lithium-ion battery cell. The CMU is also configured to compare the data indicative of the detected amount of the vented gas to a predetermined threshold amount of the subject vented gas programmed into the CMU. The CMU is further configured to trigger a signal indicative of impending failure of the lithium-ion battery cell when the detected amount of the vented gas exceeds the predetermined threshold amount of the subject vented gas.

The CMU may be further configured to determine when the lithium-ion battery cell is connected to a battery charger. In such an embodiment, the CMU may be additionally configured to electrically disconnect the lithium-ion battery cell from the battery charger in response to the detected amount of the vented gas exceeding the respective predetermined threshold amount of the subject vented gas.

The CMU may also be configured to determine when the lithium-ion battery cell is connected to an electrical load. The CMU may be further configured to disconnect the lithium-ion battery cell from the electrical load in response to the detected amount of the vented gas exceeding the respective predetermined threshold amount of the subject vented gas.

The battery management system may additionally include a fire suppression system configured to put out an electrical fire. In such an embodiment, the CMU may be further configured to activate the fire suppression system in response to the detected amount of the vented gas exceeding the respective predetermined threshold amount of the subject vented gas.

The CS-FETs may be arranged on the sensor array microchip side by side in a single plane. Furthermore, each of the CS-FETs may be configured to detect one of the gases vented by the lithium-ion battery cell.

Each of the detected gases vented by the lithium-ion battery cell may be selected from a list including hydrogen ($H_2$), carbon dioxide ($CO_2$), carbon monoxide (CO), and ethylene ($C_2H_4$). Furthermore, the predetermined threshold amount programmed into the CMU may be selected from 10 ppm for $H_2$, 500 ppm for $CO_2$, 10 ppm for CO, and 10 ppm for $C_2H_4$.

The lithium-ion battery cell may be part of a multi-cell rechargeable energy storage system (RESS) having a plurality of lithium-ion battery cells arranged in individual battery modules. In such an embodiment, the sensor array microchip may be arranged within the RESS and proximate an individual battery module. Furthermore, the sensor array microchip may be configured to detect multiple distinct gases vented by the lithium-ion battery cell on a module level.

The lithium-ion battery cell may include a housing having an exhaust port configured to vent the gases. In such an embodiment, the sensor array microchip may be arranged proximate the exhaust port.

The lithium-ion cell housing may be configured as one of a pouch, a prismatic casing, and a cylindrical casing.

A method of managing operation and detecting impending failure of a lithium-ion battery cell, using the battery management system as described above, is also disclosed.

The above features and advantages, and other features and advantages of the present disclosure, will be readily apparent from the following detailed description of the embodiment(s) and best mode(s) for carrying out the described disclosure when taken in connection with the accompanying drawings and appended claims.

DETAILED DESCRIPTION

Figure 1:
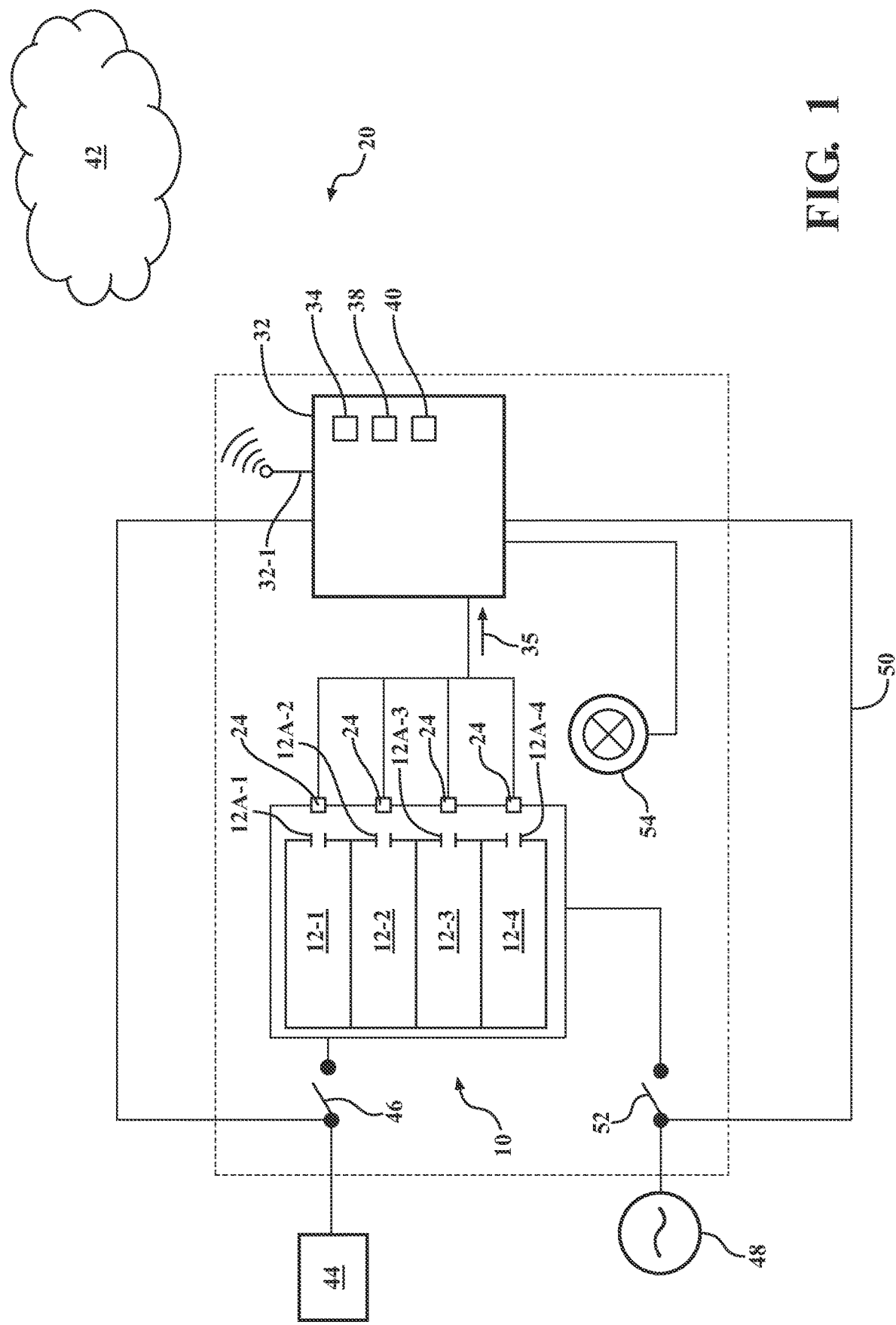
FIG. 1 is a circuit diagram of a multi-cell rechargeable energy storage system (RESS) having rechargeable lithium-ion (Li-ion) battery cells connected to a battery management system (BMS) equipped with sensor array microchips using silicon chemical-sensitive field effect transistors (CS-FETs) for detecting multiple distinct gases vented by the battery cells, according to the present disclosure.

Referring to FIG. 1, a multi-cell rechargeable energy storage system (RESS) 10. The RESS 10 includes individual battery modules 12 each having one or more rechargeable lithium-ion battery cells 14 (shown in FIG. 2). The RES S 10 is configured to generate and store electrical energy through heat-producing electro-chemical reactions for supplying the electrical energy to power an electrical load. In battery modules 12 having a plurality of Lithium ion (Li-ion) cell battery cells 14, the subject cells may be arranged, i.e., connected, either in series or in parallel. A plurality of such modules 12 may then be arranged in a battery pack as part of the RESS 10. Although four modules 12-1, 12-2, 12-3, 12-4 are shown, nothing precludes the RESS 10 from having a greater number of such battery modules. A generalized version of the RESS 10 shown in FIG. 1, with its Li-ion battery cells 14, may be used to power various products, for example, electric vehicles and consumer electronic devices, such as smartphones and laptops.

Figure 2:
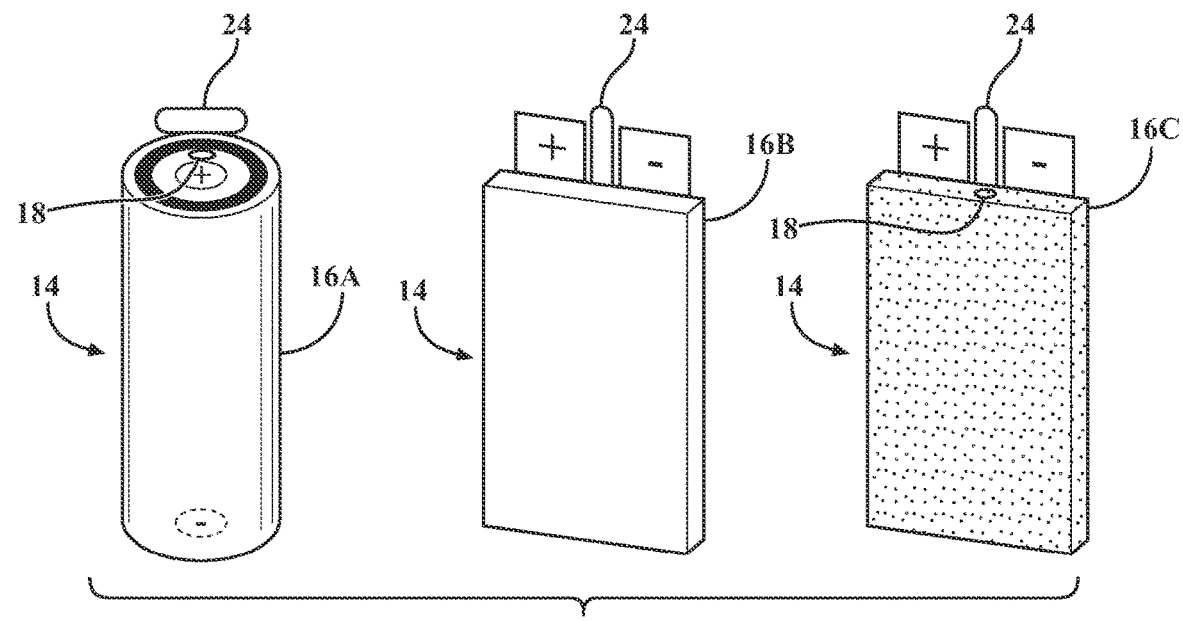
FIG. 2 is a schematic side view of three exemplary embodiments of the Li-ion battery cell shown in FIG. 1.

FIG. 2 depicts three exemplary embodiments of Li-ion battery cell 14. Each of the subject embodiments of the Li-ion battery cell 14 includes a housing configured to encase a respective negative electrode or anode, a positive electrode or cathode, as well as battery's electrolyte, gasket(s), etc. Specifically, the respective housings of the three battery cells 14 shown in FIG. 2, include a cylindrical casing 16A, generally configured as a hard metal container, a pouch 16B configured as a relatively flexible laminate material container, and a prismatic casing 16C configured as a rigid, parallelogram shaped container. Each of the subject embodiments of the housing 16 may include an exhaust port 18, such as an opening or a chimney configured to vent gases emitted by the Li-ion battery cell 14. A battery cell 14 having a cylindrical casing 16A may have a dedicated exhaust port 18 configured as a vent opening or a chimney. On the other hand, battery cells 14 having either a pouch 16B or a prismatic casing 16C may be non-vented. In such pouch or prismatic battery cells, trace gas is generally detected when sealing of the housing 16 has failed and the battery has begun to operate at reduced capacity.

With resumed reference to FIG. 1, the RESS 10 is operatively connected to a battery management system (BMS) 20. The BMS 20 is configured to regulate operation of the RESS 10, and, particularly, to detect malfunction and impending failure of the Li-ion battery cell(s) 14. In other words, the BMS 20 is designed and constructed to perform early detection of, as well as issue a warning with regard to, failure of Li-ion batter cell(s) 14. When undergoing high internal reaction rates, lithium-ion battery cells 14 may generate significant amounts of thermal energy, which may lead to a thermal runaway event and catastrophic cell failure. In general, the term "thermal runaway event" refers to an uncontrolled increase in temperature in a battery system. During a thermal runaway event, the generation of heat within a battery system or a battery cell exceeds the dissipation of heat, thus leading to a further increase in temperature. Generally, a thermal runaway event may be triggered by various conditions, including a short circuit within the cell, improper cell use, physical abuse, manufacturing defects, or exposure of the cell to extreme external temperatures.

Figure 3:
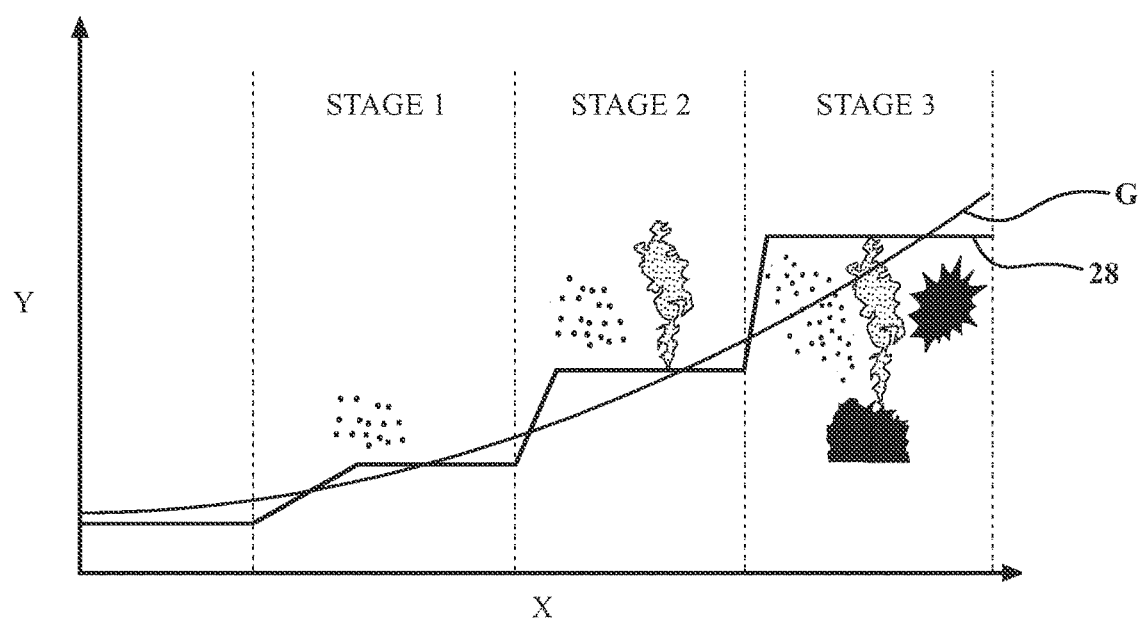
FIG. 3 is a data plot illustrating an amount of gas a typical Li-ion battery cell vents leading up to battery cell failure as a function of time.

Li-ion battery cells, such as the battery cells 14, are particularly known to emit or vent gases such as hydrogen ($H_2$), carbon dioxide ($CO_2$), carbon monoxide (CO), ethylene ($C_2H_4$) while undergoing a thermal chain reaction, in advance to catastrophic battery failure. As shown in FIG. 3, the amount of gas a typical Li-ion battery cell vents leading up to battery cell failure is described by a curve G, wherein the X-axis in the graph represents time and Y-axis represents the amount of a particular gas vented by the battery cell. The increase in the vented amount of gas described by the curve G may be broken up into three general categories or stages. In Stage 1, the amount of emitted gas may be qualified as a trace. In Stage 2, the amount of emitted gas may be qualified as a moderate and is generally accompanied by visible smoke. In Stage 3, the amount of emitted gas may be qualified as a significant or abundant and is generally accompanied by thermal runaway, battery cell failure, and shortly by visible fire and an explosion.

With resumed reference to FIG. 1, the BMS 20 includes one or more multi-gas sensor array system on chips (SoC) or microchips 22 (shown in FIGS. 1, 2, 4, and 5). Each microchip 22 may be arranged proximate the exhaust port 18 in either of the embodiments of the Li-ion battery cell 14, as shown in FIG. 2. As noted above, the Li-ion battery cell 14 may be part of an RESS 10 having a plurality of analogous Li-ion battery cells 14 arranged in individual battery modules 12. Accordingly, in such an embodiment, the BMS 20 may include multiple microchips 22, one microchip for each battery cell 14, for example, as shown in FIG. 2. Alternatively, as shown in FIG. 1, each of the microchips 22 may be arranged in a central position relative to or inside an individual battery module 12-1, 12-2, 12-3, 12-4, such as proximate to or inside a respective module exhaust opening 12A-1, 12A-2, 12A-3, 12A-4 to detect multiple distinct gases vented by the Li-ion battery cell 14 on a module level. In other words, in such an embodiment each microchip 22 may be arranged to detect gases vented by one or a plurality of Li-ion battery cells 14 situated in a particular battery module 12.

Figure 4:
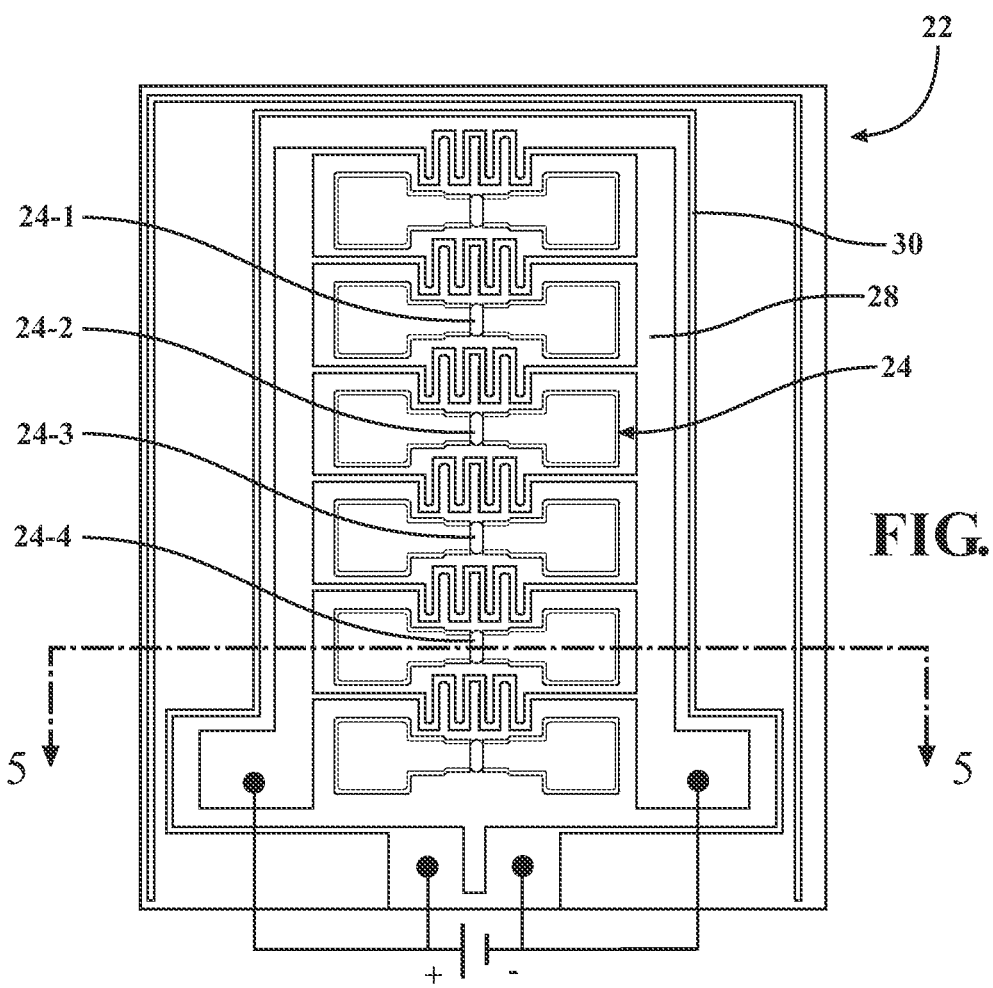
FIG. 4 is a schematic top view of an individual microchip shown in FIG. 1, depicting a plurality of CS-FETs along with micro-heaters and a temperature sensor, according to the present disclosure.
Figure 5:
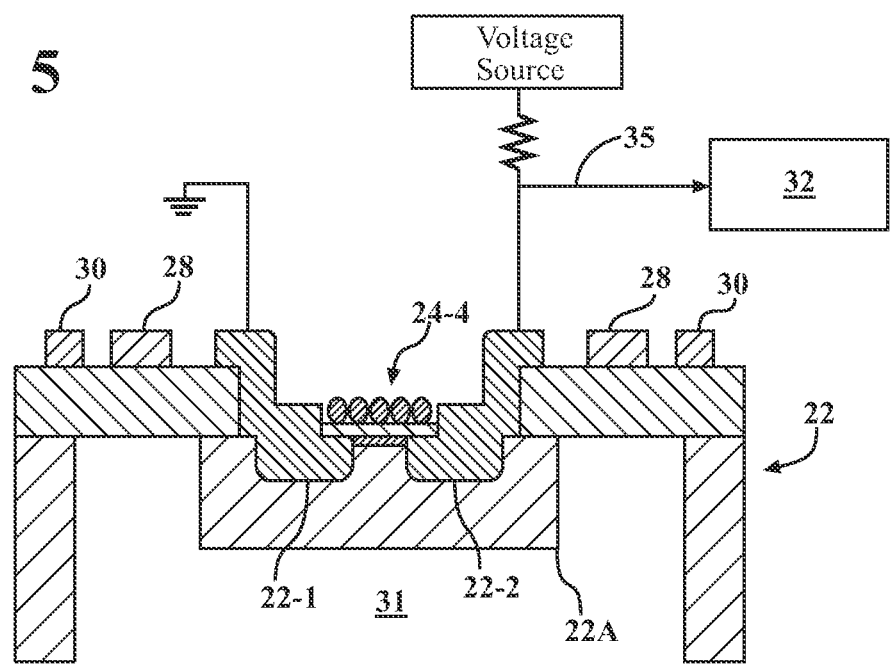
FIG. 5 is a schematic cross-sectional side view of the microchip shown in FIG. 4, specifically depicting one of the individual CS-FETs, according to the present disclosure.

As shown in FIGS. 4 and 5, the microchip 22 includes a plurality of silicon chemical-sensitive field effect transistors (CS-FETs). The CS-FETs 24 are configured to detect functionally significant amounts of multiple chemically distinct gases vented by the Li-ion battery cell(s) 14. Each of the individual CS-FETs 24 is configured to detect one of the gases vented by the Li-ion battery cell 14. Each individual CS-FETs 24 is differentiated from the other CS-FETs by a distinct nano-material catalyst element, depicted in FIG. 4 as elements 24-1, 24-2, 24-3, and 24-4. In a cross-sectional plane 5-5 indicated in FIG. 4, FIG. 5 specifically depicts a schematic section of an individual sensor 24-4 mounted on the microchip 22. Within a single CS-FET 24, the nano-material catalyst element, either 24-1, 24-2, 24-3, or 24-4, is responsible for interaction with the vented gas. The respective nano-material catalyst elements 24-1, 24-2, 24-3, and 24-4 may be constructed from metals like Platinum (for detecting $C_2H_4$ gas), Palladium-Platinum (for detecting CO gas), or mixtures of metals like Nickel-Palladium (for detecting $H_2$ gas), and Gold-Copper (for detecting $CO_2$ gas). The thickness of each nano-material catalyst element may be in a range of 1-10 nm.

As shown in FIG. 5, the microchip 22 includes a silicon transistor body 22A for supporting the respective nano-material catalyst elements 24-1, 24-2, 24-3, and 24-4. As additionally shown, the silicon transistor body 22A forms localized silicon islands to support a plurality of source terminals 22-1, one for each nano-material catalyst element 24-1, 24-2, 24-3, and 24-4, connected to ground. The silicon transistor body 22A also supports a plurality of drain terminals 22-2, each connecting a respective nano-material catalyst element 24-1, 24-2, 24-3, and 24-4 to a power source, via a digital or an analog converter (not shown). The nano-material catalyst elements 24-1, 24-2, 24-3, and 24-4 are electrically isolated from one another and are not connected to an electric voltage source. Each nano-material catalyst 24-1, 24-2, 24-3, and 24-4 is specifically configured to interact with and detect a specific gas without interference from other gases as a result of the subject catalyst's particular material properties.

Functionally, each CS-FET 24 embedded in the silicon transistor body 22A is analogous to a silicon electronic transistor. Generally, an electronic transistor has three electrodes, a source electrode, a gate electrode, and a drain electrode. The source electrode supplies the charge carriers to the transistor. The drain electrode collects or drains charge carriers or electrons. Charge carriers generally flow from the source electrode to the drain electrode upon application of a voltage across the drain to the source. The role of the gate electrode is to control this flow of the charge carriers, where the flow is regulated by the amount of voltage applied to the gate.

Operation of each CS-FET 24 is similar to the above-described electronic transistor, except that the flow of charge carriers from the source electrode to the drain electrode is controlled by an interaction between the particular gate electrode and a specific gas, rather than an application of a fixed electric voltage to the gate. More specifically, in each CS-FET 24, the respective nano-material catalyst 24-1, 24-2, 24-3, and 24-4 operates as the gate electrode, which is not connected to an electric voltage source. When a specific gas chemically interacts with the particular nano-material catalyst, a phenomenon generally described as "work-function change" is induced in the subject nano-material catalyst. The generated work-function change in turn changes the flow of charge carriers from the source to the drain, leading to a detection event of the vented gas.

An interaction between a specific gas and the particular nano-material catalyst 24-1, 24-2, 24-3, or 24-4 leads to modulation or changes in electrical current flowing from the respective source terminal to the respective drain terminal in the silicon transistor body 22A. The microchip 22 may additionally include micro-heater(s) 28 and temperature sensor(s) 30, each arranged around the periphery of the individual CS-FETs 24. The micro-heaters 28 and temperature sensors 30 serve a dual purpose: 1) maintaining constant microchip temperature relative to the ambient, and 2) minimizing ambient humidity interference. The micro-heaters 28 and temperature sensors 30 may be constructed from thin films of metals like tungsten, gold-titanium, or polysilicon with thicknesses in a range of 50-500 nm. As shown in a cross-sectional plane 5-5 indicated in FIG. 4 and depicted in FIG. 5, the microchip 22 may include a recessed cavity 31 configured to minimize micro-heater thermal losses and overall microchip power consumption.

As also shown in FIG. 4, individual CS-FETs 24 may be arranged on the sensor array microchip 22 side by side in a single plane. Particularly, the individual CS-FETs 24 are arranged substantially parallel relative to each other. Each of the multiple nano-material catalyst 24-1, 24-2, 24-3, 24-4 is sensitive to, i.e., configured to detect, one of the gases vented by the lithium-ion battery cell 14. Specifically, the individual nano-material catalysts 24-1, 24-2, 24-3, 24-4 may be configured to detect, in no particular order, vented gases such as hydrogen, carbon dioxide, carbon monoxide, and ethylene. Although four individual nano-material catalysts 24-1, 24-2, 24-3, 24-4 are shown, nothing precludes construction of the microchip 22 with a smaller or greater number (as indicated by two additional, unoccupied sensor spaces in FIG. 4) of individual nano-material catalysts.

With continued reference to FIG. 1, the BMS 20 also includes an electronic cell monitoring unit (CMU) 32 in operative communication with the CS-FETs 24. The CMU 32 may be part of a battery controller network (not shown) configured to manage operation of the battery modules 12. Among various communication, processing, and management functions, the CMU 32 is configured, i.e., constructed and programmed, to receive from the CS-FETs 24 data 35 indicative of the detected amount or level of at least one of the gases vented by the Li-ion battery cell(s) 14. The data signal 35 generated by the microchip 22 may first be transmitted to an analog or digital converter (not shown) and then on to the CMU 32. The signal transmitted by each of the CS-FETs 24 indicative of the data 35 may represent discrete stages, i.e., Stage 1, Stage 2, and Stage 3, in gas emission shown in FIG. 3, or corresponding to specifically detected amount of a particular vented gas. The transmitted data 35 is shown superimposed over the curve G in FIG. 3 to illustrate how the amounts detected and transmitted to the CMU 32 corresponds to the three stages of increase in the amount of vented gas.

The microchip 22, including the CS-FETs 24, may be physically wired to the particular CMU 32 (as shown in FIG. 1, or communicate with the CMU wirelessly. To affect wireless communication, the CMU 32 may include an antenna 32-1 for receiving the data 35 from the microchip 22, for which purpose each microchip may also be equipped with a respective antenna (not shown). To support requisite management of the battery modules 12, the CMU 32 specifically includes a processor and tangible, non-transitory memory, which includes instructions for operation of the BMS 20 programmed therein. The memory may be an appropriate recordable medium that participates in providing computer-readable data or process instructions. Such a recordable medium may take many forms, including but not limited to non-volatile media and volatile media.

Non-volatile media for the CMU 32 may include, for example, optical or magnetic disks and other persistent memory. Volatile media may include, for example, dynamic random access memory (DRAM), which may constitute a main memory. The instructions programmed into the CMU 32 may be transmitted by one or more transmission medium, including coaxial cables, copper wire and fiber optics, including the wires that comprise a system bus coupled to a processor of a computer, or via a wireless connection. Memory of the CMU 32 may also include a flexible disk, hard disk, magnetic tape, another magnetic medium, a CD-ROM, DVD, another optical medium, etc. The CMU 32 may be configured or equipped with other required computer hardware, such as a high-speed clock, requisite Analog-to- Digital (A/D) and/or Digital-to-Analog (D/A) circuitry, input/output circuitry and devices (I/O), as well as appropriate signal conditioning and/or buffer circuitry. Algorithm(s), indicated generally via numeral 34, required by the CMU 32 or accessible thereby may be stored in the memory of the CMU 32 and automatically executed to facilitate operation of the BMS 20. Specifically, the algorithm(s) 34 may include an inventory mode configured to monitor the CS-FETs 24 and/or interrogate the CS-FETs at predetermined time intervals to verify effective line of communication with and operation of the CS-FETs.

The CMU 32 is also specifically configured to compare the received vented gas data 35 to a respective predetermined threshold amount 38 of the subject vented gas. The predetermined threshold amounts 38 of the subject vented gases may be determined empirically during testing of representative Li-ion battery cells, such as the battery cell 14, and programmed into the CMU 32. The CMU 32 is additionally configured to trigger a signal 40 indicative of a battery fault and predictive of a thermal runaway, i.e., impending failure of the Li-ion battery cell(s) 14, when the detected amount(s) of the gases(s) vented by the lithium-ion battery cell exceeds the predetermined threshold amount 38 of the subject vented gas. The respective predetermined threshold amount 38 programmed into the CMU 32 may be 10 ppm (parts per million) for $H_2$, 500 ppm for $CO_2$, 10 ppm for CO, and 10 ppm for $C_2H_4$ for individual the Li-ion battery cells 14. In the embodiment of the BMS 20 shown in FIG. 1, the respective predetermined threshold amounts 38 programmed into the CMU 32 may be adjusted to account for the specific number of the Li-ion battery cells 14 in the particular battery module 12. In either embodiment, the CMU 32 may trigger the signal 40 when the detected amount of at least one of the vented gases exceeds the respective threshold amount 38.

The signal 40 may be an audible and/or visual sensory signal or alert. For example, the signal 40 may be an audible indicator, such as a high decibel and/or frequency alarm. The signal 40 may also be a visual indicator, such as a malfunction indicator light (MIL) a generated digital malfunction code stored within the memory of the CMU 32. The digital malfunction code stored within the memory of the CMU 32 may be retrieved by an authorized technician or communicated to a central authority including a database, such as an IT cloud server 42 (shown in FIG. 1). As shown, the IT cloud server 42 is arranged remotely from and in wireless communication with the CMU 32, such as via the antenna 32-1, and/or with the RESS 10, thus enabling centralized system access and management. In such an embodiment, the external IT cloud server 42 may be part of the BMS 20 overseeing a network of multi-cell rechargeable energy storage systems, such as the RESS 10, with individual CMU's, analogous to the CMU 32. Requisite communication between the respective CMU's and the IT cloud server 42 may be cellular or via wireless local area networking (Wi-Fi) facilitated by a cloud edge residing on a cellular base station for reduced latency, or via an earth-orbiting satellite (not shown).

The CMU 32 may be additionally configured to detect when the particular Li-ion battery cell 14 is electrically connected to a battery charger 44, i.e., receiving charge current therefrom. The CMU 32 may be further configured to electrically disconnect the Li-ion battery cell 14 from the battery charger 44 in response to the detected amount of the gas(s) vented by the subject battery cell, represented by the data 35, exceeding the predetermined threshold amount(s) 38 of the subject vented gas(s). The CMU 32 may be configured to disconnect the battery charger 44 in parallel with or in response to the triggering or setting of the signal 40. Disconnection of the battery charger 44 may be effected via opening a switch 46 in the circuit connecting the charger to the Li-ion battery cell 14.

The CMU 32 may be additionally configured to detect when the Li-ion battery cell 14 is connected to an electrical load 48, for example a vehicle subsystem, such as a heating, ventilation, and air conditioning (HVAC) system or a traction motor (not shown). Particularly, when employed in a motor vehicle, the RESS 10 may be connected to the electrical load 48 and the CMU 32 via a high-voltage BUS 50 (shown in FIG. 1). In such an embodiment, the CMU 32 may be further configured to disconnect the Li-ion battery cell 14 from the electrical load 48 in response to the detected amount of the gas(s) vented by the Li-ion battery cell, represented by the data 35, exceeding the predetermined threshold amount(s) 38 of the subject vented gas(s). Disconnection of the electrical load 48 may be affected via opening a switch 52 in the circuit connecting the load to the Li-ion battery cell 14. Similar to the above-described situation with disconnection of the charger 44, the CMU 32 may be configured to disconnect the electrical load 48 in parallel with or in response to the triggering or setting of the signal 40.

The BMS 20 may also include a fire suppression system 54 configured to put out an electrical fire. The fire suppression system 54 may, for example, include a sprinkler system having a water or foam supply system providing adequate pressure and flow-rate to a fluid distribution piping system, connected to individual sprinkler units (not shown). Another example of the fire suppression system 54 may utilize strategically arranged canisters configured to automatically dispense propellant inert gases and ultra-fine aerosol particles to put out electrolyte fires, prevent re-flashes, and reduce the risk of battery enclosure explosions. The CMU 32 may be configured to activate the fire suppression system 54 in response to the detected amount of the gas(s) vented by the Li-ion battery cell 14 exceeding the predetermined threshold amount(s) 38 of the subject vented gas(s).

Overall, the multi-gas sensor array microchip 22 with the CS-FETs 24 is used to detect vented gases from Li-ion battery cells 14 to achieve early warning in case of Li-ion battery failure. Compared to existing gas sensing technologies, the multi-gas sensor array microchip 22 incorporated into the BMS 20 of the present disclosure provides a significantly more sensitive and cost-effective approach to detection of impending Li-ion battery cell 14 malfunction. The disclosed approach programmed into the CMU 32 may be employed to provide enhanced safety of individual Li-ion battery cells 14 and Li-ion battery modules 12 and facilitate protection against catastrophic failure, fire, and explosion of Li-ion battery cells.

Figure 6:
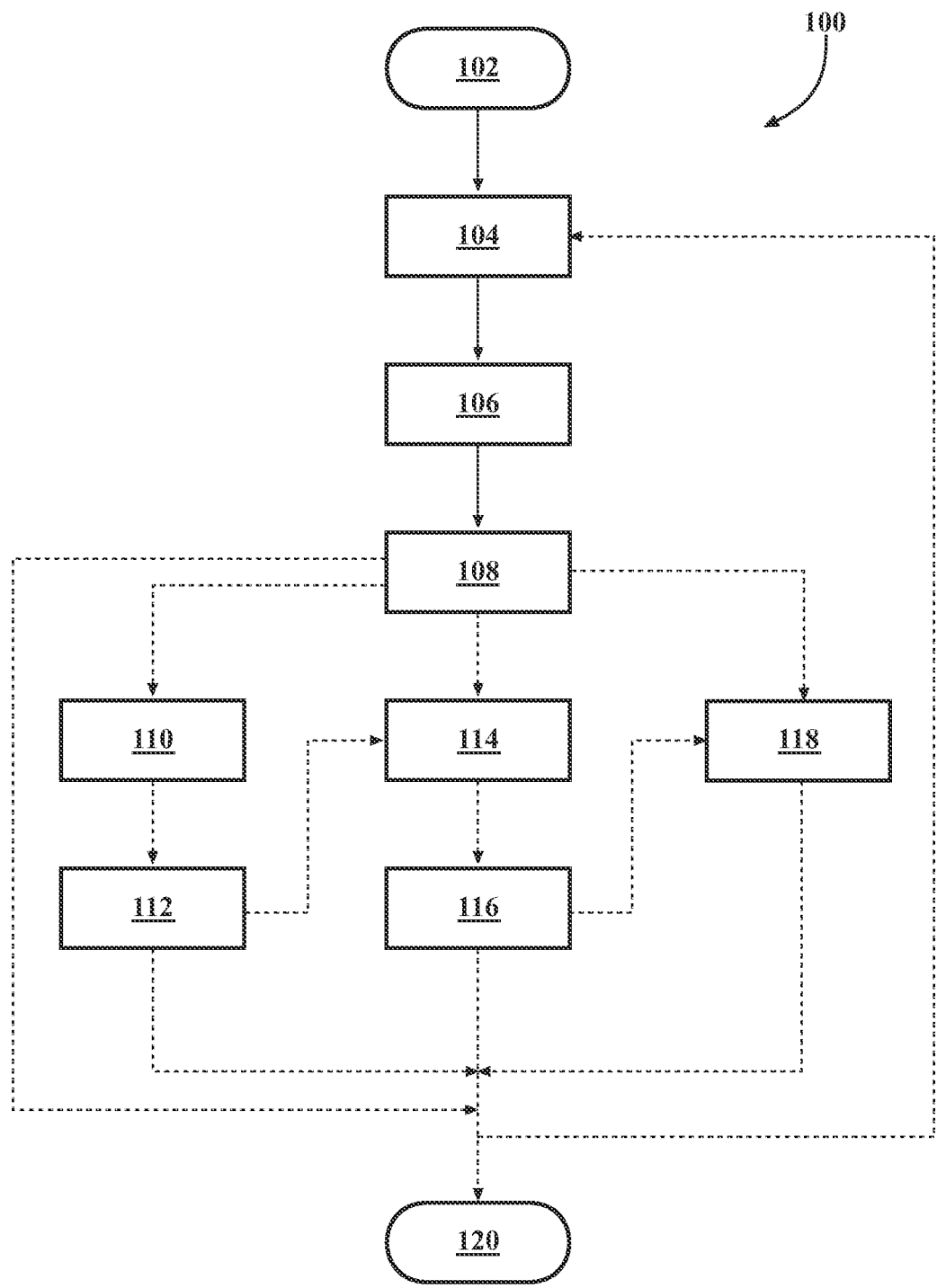
FIG. 6 illustrates a method of managing operation and detecting impending failure of a Li-ion battery cell using the BMS shown in FIGS. 1-5.

A method 100 of managing operation and detecting impending failure of Li-ion battery cell(s) 14 via the BMS 20 is shown in FIG. 6 and described below with reference to the structure shown in FIGS. 1-5. Method 100 commences in frame 102 with detecting, via the CS-FET(s) 24 arranged on the microchip 22, at least one of multiple distinct gases vented by the Li-ion battery cell(s) 14. Following frame 102, the method advances to frame 104. In frame 104, the method includes receiving from the CS-FET(s) 24, via the CMU 32, the data 35 indicative of the amount of the detected gas(s) vented by at least one of the Li-ion battery cells 14. From frame 104, the method moves on to frame 106, where the method includes comparing, via the CMU 32, the data 35 indicative of the amount of the detected vented gas to the respective predetermined threshold amount 38 of the subject vented gas programmed into the CMU. As described with respect to FIGS. 1-5, the predetermined threshold amount 38 programmed into the CMU 32 may be selected from 10 ppm for $H_2$, 500 ppm for $CO_2$, 10 ppm for CO, and 10 ppm for $C_2H_4$.

After frame 106 the method proceeds to frame 108. In frame 108, the method includes triggering, via the CMU 32, the signal 40 indicative of impending failure of the Li-ion battery cell(s) 14 when the detected amount of a particular gas vented by the Li-ion battery cell(s) 14, represented by the data 35, exceeds the respective predetermined threshold amount 38 of the subject vented gas. Following frame 108, the method may proceed to frame 110. In frame 110, the method may include determining or detecting, via the CMU 32, when the Li-ion battery cell(s) 14 are connected to the battery charger 44 and drawing electrical current therefrom. After the determination that the Li-ion battery cell(s) 14 are connected to the battery charger 44, the method may advance to frame 112. In frame 112, the method may include electrically disconnecting, via the CMU 32, the Li-ion battery cell(s) 14 from the battery charger 44 in response to the detected amount of the vented gas exceeding the respective predetermined threshold amount 38.

Alternatively, following either of the frames 108 or 112, the method may proceed to frame 114. In frame 114, the method may include determining or detecting, via the CMU 32, when the Li-ion battery cell(s) 14 are connected to the electrical load 48. After the determination that the Li-ion battery cell(s) 14 are connected to the electrical load 48, the method may advance to frame 116. In frame 116, the method may include electrically disconnecting, via the CMU 32, the Li-ion battery cell(s) 14 from the electrical load 48 in response to the detected amount of the vented gas exceeding the respective predetermined threshold amount 38. Following either of the frames 108, 112, or 116, the method may proceed to frame 118. In frame 118, the method may include activating, via the CMU 32, the fire suppression system 54 in response to the detected amount of the vented gas exceeding the respective predetermined threshold amount 38.

Accordingly, as envisioned, the method 100 enables continuous monitoring the Li-ion battery cell(s) 14 for detecting impending failure of the subject Li-ion battery cell(s), and further issuing an alert in the event such a condition is ascertained. Additionally, the method 100 enables restricting the charging and discharging of the subject battery cell(s) 14, and further activating fire suppression in if such impending failure is established. Consequently, following either of the frames 108, 112, 116, or 118, the method may loop back to frame 104 for continued monitoring of the Li-ion battery cell(s) 14 via the BMS 20 and detecting gases vented by the Li-ion battery cell(s) 14 via the CS-FETs 24. Alternatively, the method may conclude in frame 120.

The detailed description and the drawings or figures are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment may be combined with one or a plurality of other desired characteristics from other embodiments, resulting in other embodiments not described in words or by reference to the drawings. Accordingly, such other embodiments fall within the framework of the scope of the appended claims.

What is claimed is:

1. A battery management system configured to detect impending failure of a lithium-ion battery cell, the battery management system comprising:
   a sensor array microchip including a plurality of silicon chemical-sensitive field effect transistors (CS-FETs) configured to detect multiple distinct gases vented by the lithium-ion battery cell, wherein each of the CS-FETs is configured to detect one of the gases vented by the lithium-ion battery cell; and
   a cell monitoring unit (CMU) in operative communication with the sensor array microchip and configured to:
      receive from at least one of the CS-FETs data indicative of a detected amount of gas vented by the lithium-ion battery cell;
      compare the data indicative of the detected amount of the vented gas to a predetermined threshold amount of the subject vented gas programmed into the CMU; and
      trigger a signal indicative of impending failure of the lithium-ion battery cell when the detected amount of the vented gas exceeds the predetermined threshold amount of the subject vented gas.

2. The battery management system of claim 1, wherein the CMU is further configured to:
   determine when the lithium-ion battery cell is connected to a battery charger; and
   electrically disconnect the lithium-ion battery cell from the battery charger in response to the detected amount of the vented gas exceeding the respective predetermined threshold amount of the subject vented gas.

3. The battery management system of claim 1, wherein the CMU is further configured to:
   determine when the lithium-ion battery cell is connected to an electrical load; and
   disconnect the lithium-ion battery cell from the electrical load in response to the detected amount of the vented gas exceeding the respective predetermined threshold amount of the subject vented gas.

4. The battery management system of claim 1, further comprising a fire suppression system configured to put out an electrical fire, wherein the CMU is further configured to activate the fire suppression system in response to the detected amount of the vented gas exceeding the respective predetermined threshold amount of the subject vented gas.

5. The battery management system of claim 1, wherein the CS-FETs are arranged on the sensor array microchip side by side in a single plane.

6. The battery management system of claim 5, wherein each of the detected gases vented by the lithium-ion battery cell is selected from a list including hydrogen ($H_2$), carbon dioxide ($CO_2$), carbon monoxide (CO), and ethylene ($C_2H_4$).

7. The battery management system of claim 6, wherein the predetermined threshold amount programmed into the CMU is selected from 10 ppm for $H_2$, 500 ppm for $CO_2$, 10 ppm for CO, and 10 ppm for $C_2H_4$.

8. The battery management system of claim 1, wherein the lithium-ion battery cell is part of a multi-cell rechargeable energy storage system (RESS) having a plurality of lithium-ion battery cells arranged in individual battery modules, wherein the sensor array microchip is arranged within the RESS and proximate an individual battery module, and wherein the sensor array microchip is configured to detect multiple distinct gases vented by the lithium-ion battery cell on a module level.

9. The battery management system of claim 1, wherein the lithium-ion battery cell includes a housing having an exhaust port configured to vent the gases, and wherein the sensor array microchip is arranged proximate the exhaust port.

10. The battery management system of claim 9, wherein the housing is configured as one of a pouch, a prismatic casing, and a cylindrical casing.

11. A method of managing operation and detecting impending failure of a lithium-ion battery cell, the method comprising:
  detecting, via at least one of a plurality of silicon chemical-sensitive field effect transistors (CS-FETs) arranged on a sensor array microchip, a gas vented by the lithium-ion battery cell, wherein each of the plurality of CS-FETs is configured to detect one of multiple distinct gases vented by the lithium-ion battery cell;
  receiving from the CS-FET, via a cell monitoring unit (CMU) in operative communication with the CS-FET, data indicative of a detected amount of the gas vented by the lithium-ion battery cell;
  comparing, via the CMU, the data indicative of the detected amount of the vented gas to a predetermined threshold amount of the subject vented gas programmed into the CMU; and
  triggering, via the CMU, a signal indicative of impending failure of the lithium-ion battery cell when the detected amount of the vented gas exceeds the predetermined threshold amount of the subject vented gas.

12. The method of claim 11, further comprising:
  determining, via the CMU, when the lithium-ion battery cell is connected to a battery charger; and
  electrically disconnecting, via the CMU, the lithium-ion battery cell from the battery charger in response to the detected amount of the vented gas exceeding the respective predetermined threshold amount of the subject vented gas.

13. The method of claim 11, further comprising:
  determining, via the CMU, when the lithium-ion battery cell is connected to an electrical load; and
  disconnecting, via the CMU, the lithium-ion battery cell from the electrical load in response to the detected amount of the vented gas exceeding the respective predetermined threshold amount of the subject vented gas.

14. The method of claim 11, further comprising activating, via the CMU, a fire suppression system in response to the detected amount of the vented gas exceeding the respective predetermined threshold amount of the subject vented gas.

15. The method of claim 11, wherein the CS-FETs are arranged on the sensor array microchip side by side in a single plane.

16. The method of claim 15, wherein each of the detected gases vented by the lithium-ion battery cell is selected from a list including hydrogen ($H_2$), carbon dioxide ($CO_2$), carbon monoxide (CO), and ethylene ($C_2H_4$).

17. The method of claim 16, wherein the predetermined threshold amount programmed into the CMU is selected from 10 ppm for $H_2$, 500 ppm for $CO_2$, 10 ppm for CO, and 10 ppm for $C_2H_4$.

18. The method of claim 11, wherein:
  the lithium-ion battery cell is part of a multi-cell rechargeable energy storage system (RESS) having a plurality of lithium-ion battery cells arranged in individual battery modules;
  the sensor array microchip is arranged within the RESS and proximate an individual battery module; and
  detecting at least one of multiple distinct gases vented by the lithium-ion battery cell includes detecting multiple distinct gases vented by the lithium-ion battery cell on a module level.

19. The method of claim 11, wherein the lithium-ion battery cell includes a housing having an exhaust port configured to vent the gases, and wherein the sensor array microchip is arranged proximate the exhaust port.

20. The method of claim 19, wherein the housing is configured as one of a pouch, a prismatic casing, and a cylindrical casing.

* * * * *